United States Patent [19]
Cox

[11] Patent Number: 5,672,150
[45] Date of Patent: Sep. 30, 1997

[54] WRIST BRACE WITH PALM SUPPORT

[76] Inventor: Michael F. Cox, 10138 Lexington Estates Blvd., Boca Raton, Fla. 33428

[21] Appl. No.: 674,717

[22] Filed: Jul. 2, 1996

[51] Int. Cl.$^6$ .............................. A61F 5/058; A61F 5/37
[52] U.S. Cl. .............. 602/21; 602/20; 128/879; 473/63
[58] Field of Search .................. 602/5, 6, 21, 58, 602/64, 20; 482/44; 473/62; 128/879

[56] References Cited

U.S. PATENT DOCUMENTS

| D. 230,894 | 3/1974 | Lehneis | 473/62 X |
|---|---|---|---|
| D. 251,337 | 3/1979 | Coon | 473/62 X |
| 2,206,404 | 4/1940 | Jones | 473/62 X |
| 2,529,786 | 11/1950 | Shaw | 2/16 X |
| 4,479,648 | 10/1984 | Alivo, Jr. | 602/21 X |
| 4,796,611 | 1/1989 | Wardlaw | 2/16 X |
| 4,925,187 | 5/1990 | Fleenor et al. | 602/6 X |

FOREIGN PATENT DOCUMENTS

| 336025 | 10/1903 | France | 482/44 |
|---|---|---|---|
| WO 95/04507 | 2/1995 | WIPO | 602/21 |

*Primary Examiner*—Richard J. Apley
*Assistant Examiner*—William LaMarca
*Attorney, Agent, or Firm*—Malin, Haley, DiMaggio & Crosby, PA

[57] ABSTRACT

An opposing force wrist brace is provided that immobilizes the wrist while permitting full use of the fingers and hand. The brace is preferably a two component brace with a top and bottom member positioned and held in place on the wrist by a suitable clamping means such as a hook and loop cinching strap. The top and bottom members are specially shaped and made of a suitable material such as injection molded or heat formed pliable thermoplastic. The top and bottom members are preferably transparent to allow observation of pressure points when the device is cinched in place.

10 Claims, 6 Drawing Sheets

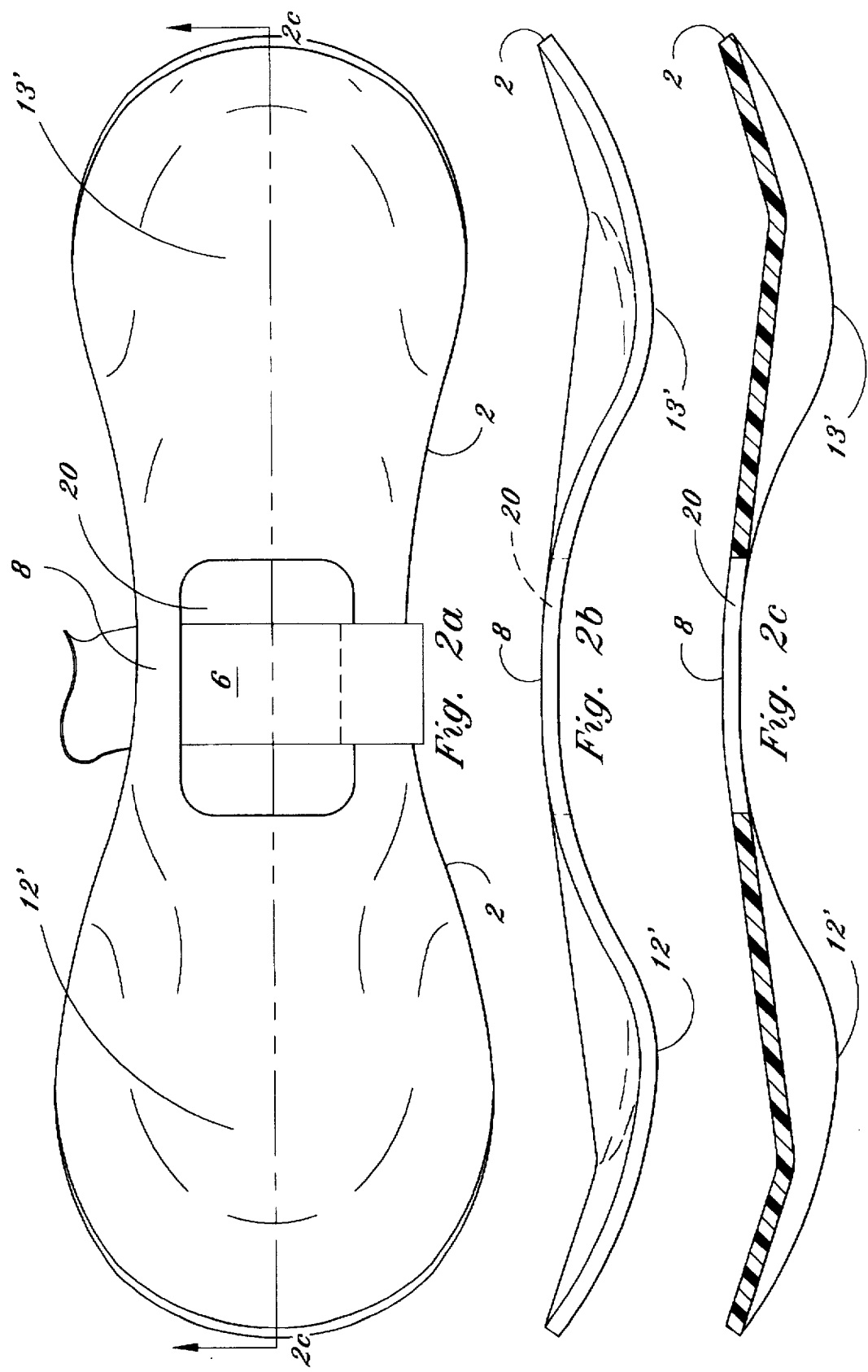

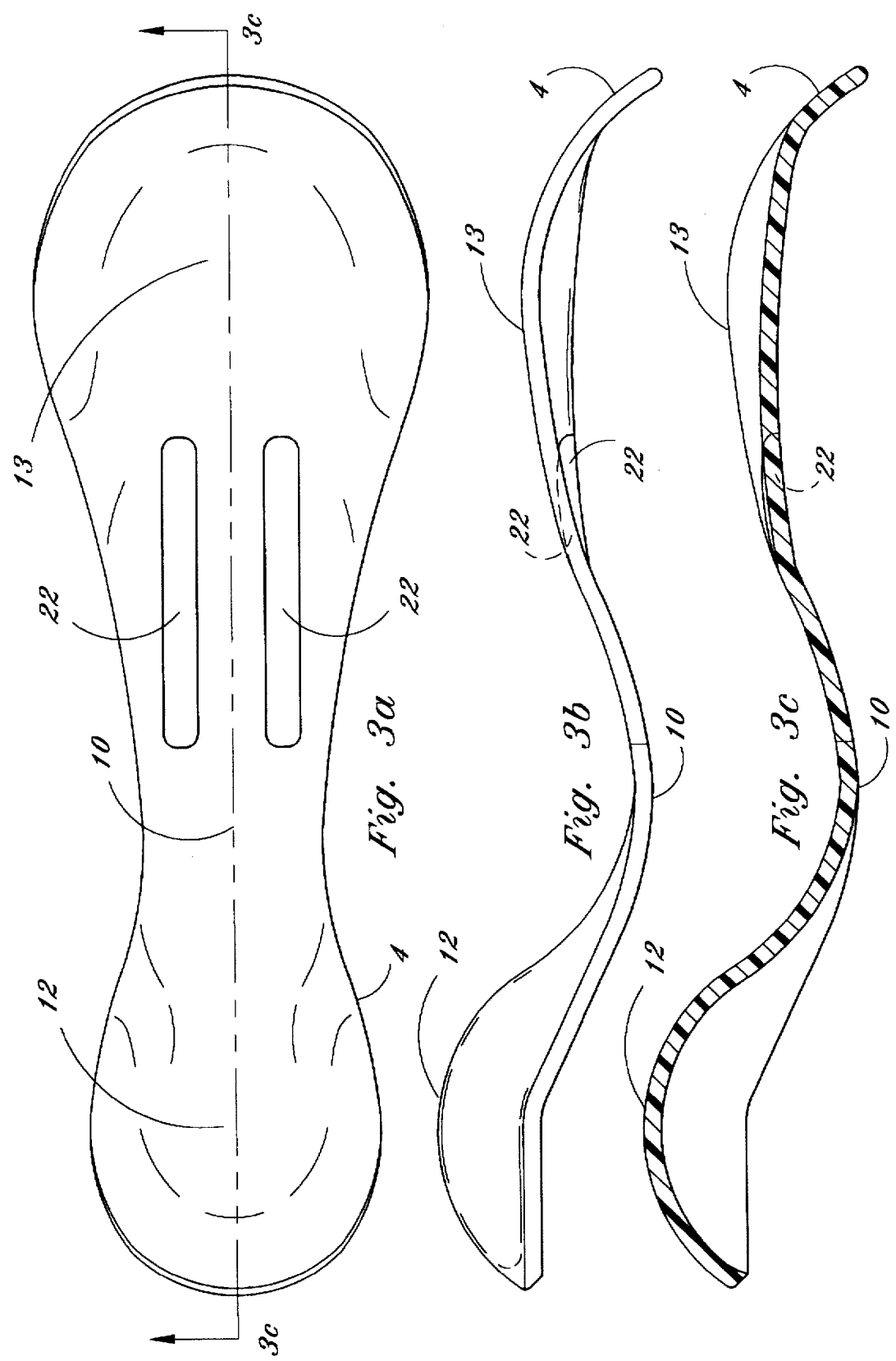

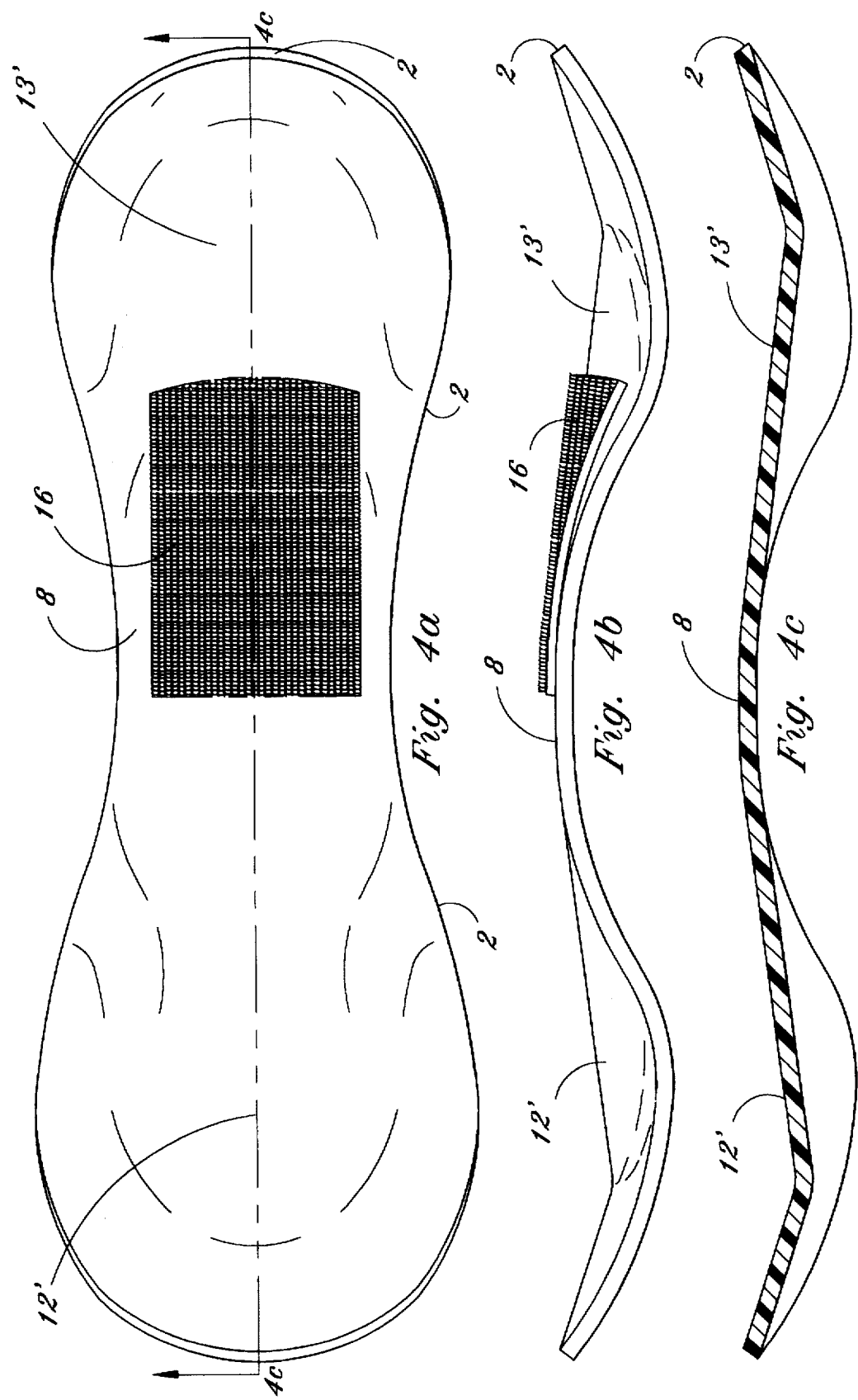

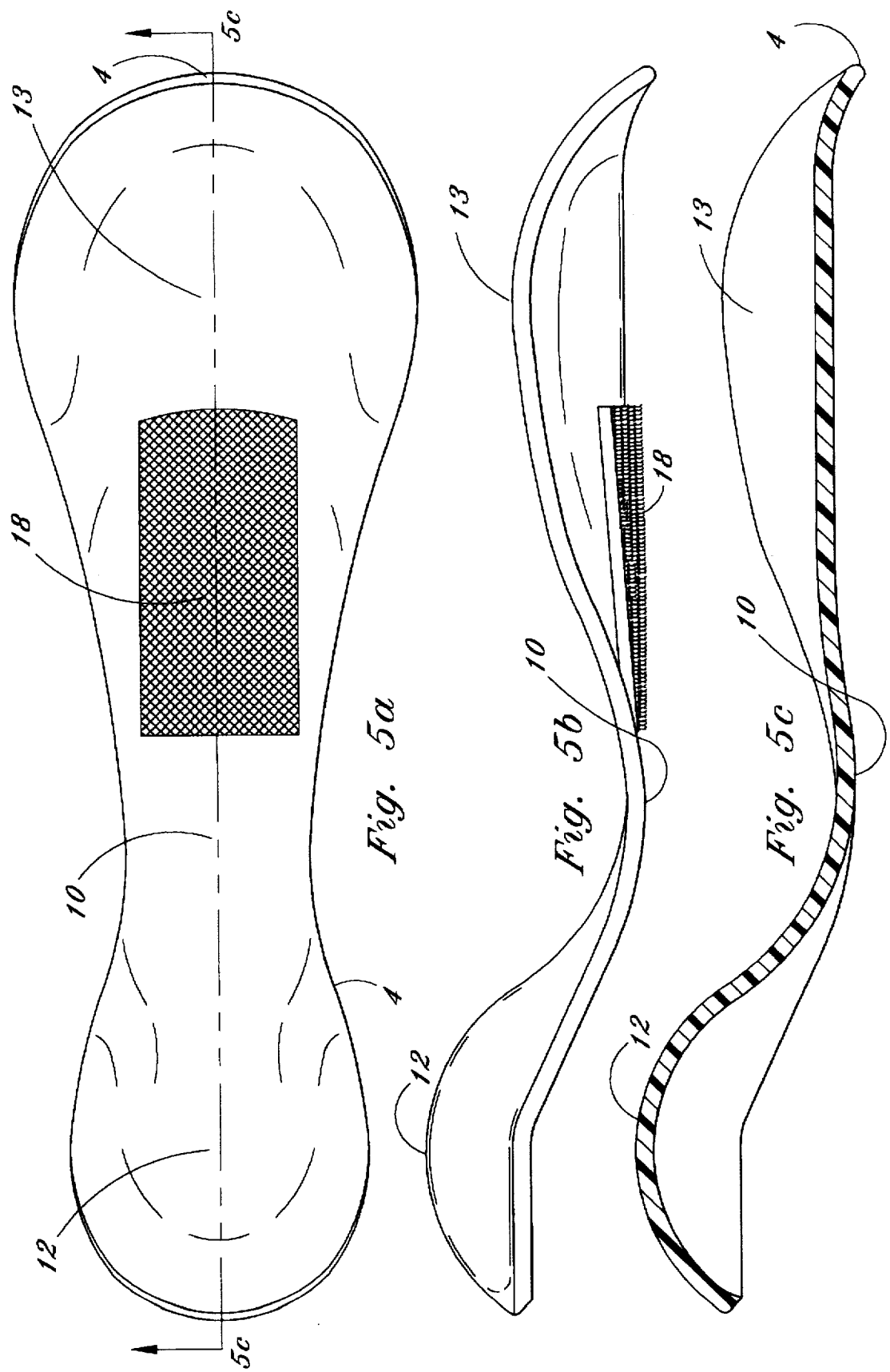

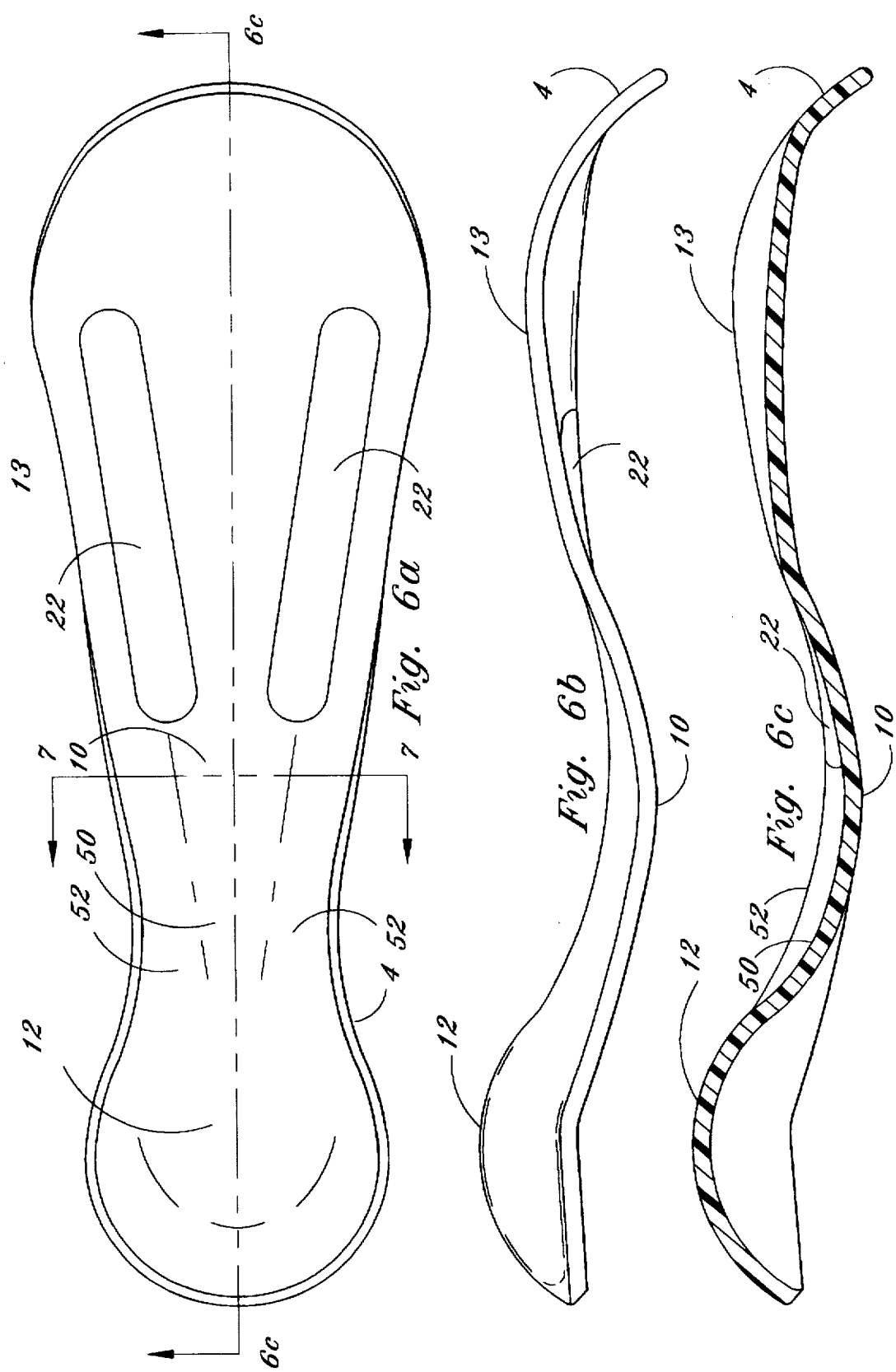

WRIST BRACE WITH PALM SUPPORT

BACKGROUND OF THE INVENTION

1. Field of the Invention

The present invention relates to a wrist brace primarily intended for immobilization of the human wrist and more particularly to an opposing force wrist brace that provides immobilization of the wrist without impeding the use of the hand and fingers.

2. Description of Related Art

Strain or overuse injury is a major problem for people that perform repetitive tasks. Most overuse injuries occur in the workplace and commonly afflict typists, computer keyboard operators, musicians, meat cutters, and others who use constant repetitive motions of the fingers, hands, or arms. This type of injury is primarily due to overuse of the muscles and/or tendons invoked during repetitive motions of a particular task.

One such injury, called Carpal Tunnel Syndrome, occurs due to prolonged flexion or extension of the wrist that causes swelling of membrane linings surrounding certain tendons. The swelling reduces the size of the Carpal Tunnel and compresses the median nerve. The result is numbness, tingling, or pain in the wrist, fingers, or forearm, with the most noticed symptom being pain.

In order to alleviate the overuse injury, aid in the recovery, or to promote preventative measures, attempts have been made to support and immobilize the wrist without pressing on the Carpal ligament, the tendons at the wrist, or the median nerve. Devices attempting to accomplish these measures range from flexible wrap-type supports to casts and splints. The primary objective of these devices is to keep the wrist immobile, as the most effective wrist support occurs when the wrist is immobilized. However, to maintain wrist immobilization, the movement of the hand and fingers is also restricted thereby discouraging the patient from following his/her normal pursuits.

There exists a need for a device that can provide wrist immobility while simultaneously permitting full use of the fingers and hand. The device preferably would be light, easy to apply, easily adjustable such that one size fits all, and capable of being worn on either hand. The device should be usable during sleep and during physical activity while in the home or workplace. The device should be usable, during repetitive tasks, to prevent an overuse injury from occurring, or to prevent aggravation of an injury.

SUMMARY OF THE INVENTION

The present invention provides an opposing force wrist brace that immobilizes the wrist while permitting full use of the fingers and hand. The brace is preferably a two component brace with top and bottom members positioned and held in place on the wrist by a suitable adjustable clamp such as a strap having hook and loop fasteners.

The top and bottom members of the present invention are strategically shaped and made of a suitable material such as injection molded or heat formed pliable thermoplastic. The top and bottom members are preferably transparent to allow observation of pressure points when the device is cinched in place, and permits viewing of watches or jewelry.

The bottom member has a dome portion at one end that nests comfortably in the palm of the hand. The dome is preferably approximately 1½ inches high. The bottom member has an arched section near its center that arches away from the under-portion of the wrist at the wrist's bending point.

The top member has an arched section near its center that arches above the wrist at the wrist's bending point. The opposing arches in the top and bottom members are each approximately ½ inch high.

When the opposing arches, which are positioned above and below the wrist, are cinched with a cinching means, such as a hook and loop strap, a spring like action is created at the wrist. The spring like action causes opposing sections of the top and bottom members, located on either side of the arched sections, to exert a clamping force on either side of the wrist's bending point. The resultant clamping forces that are exerted in front of and behind the wrist's bending point immobilizes the wrist while permitting full movement of the fingers, and use of the hand.

The clamping forces of the present invention immobilize the bending portion of the wrist which maintains the hand in a neutral and parallel orientation with the forearm. The clamping force exerted upon the hand comes from the top of the domed portion of the bottom member being pressed toward the corresponding portion on the top member. This clamping force along with the clamping force exerted upon the forearm, immobilizes the hand in relation to the wrist and forearm. The shape of the specially designed domed or spherical portion of the bottom member permits full movement of the fingers while keeping the wrist immobile. The special domed shape in the palm in conjunction with full use of the fingers permits the hand to be used in a normal fashion while the invention is being worn.

The top and bottom members are movable for adjustment and hook into place on the hook and loop cinching strap to accommodate most wrist sizes. The entire device is lightweight, and can be easily washed and dried.

Accordingly it is an objective of the present invention to provide a comfortable wrist brace that immobilizes the wrist while permitting full use of the hand and fingers.

It is a further objective of the present invention to provide a wrist brace that is lightweight, transparent, and easily cleaned.

It is still a further objective of the present invention to provide a wrist brace that easily attaches and is adjustable to fit most wrist sizes.

It is yet another objective of the present invention to provide a wrist brace that has top and bottom members that are shaped, pliable, and made from a thermoplastic material.

It is another objective of the present invention to provide a wrist brace that has a top and bottom members that are cinched together by a hook and loop strap.

It is still another objective of the present invention to provide a wrist brace that can be worn on either the left or right hand.

In accordance with these and other objects which will become apparent hereinafter, the instant invention will now be described with particular reference to the accompanying drawings.

BRIEF DESCRIPTION OF THE DRAWINGS

FIG. 2a is a top plan view of the top member of the present invention.

FIG. 2b is a side elevational view of the top member shown in FIG. 2a.

FIG. 2c is a side elevational view in cross-section taken along line 2c—2c of FIG. 2a.

FIG. 3a is a bottom plan view of the bottom member of the present invention.

FIG. 3b is a side elevational view of the bottom member shown in FIG. 3a.

FIG. 3c is a side elevational view in cross-section taken along line 3c—3c of FIG. 3a.

FIGS. 4a–4c and FIGS. 5a–5c show an alternate embodiment of the present invention and correspond to the views shown in FIGS. 2a–2c and FIGS. 3a–3c.

FIGS. 6a–6c show an alternate embodiment of that shown in FIGS. 3a–3c.

FIG. 7 shows a rear elevational view in cross section taken along line 7—7 in FIG. 6a.

DESCRIPTION OF THE PREFERRED EMBODIMENTS

Figure 1:
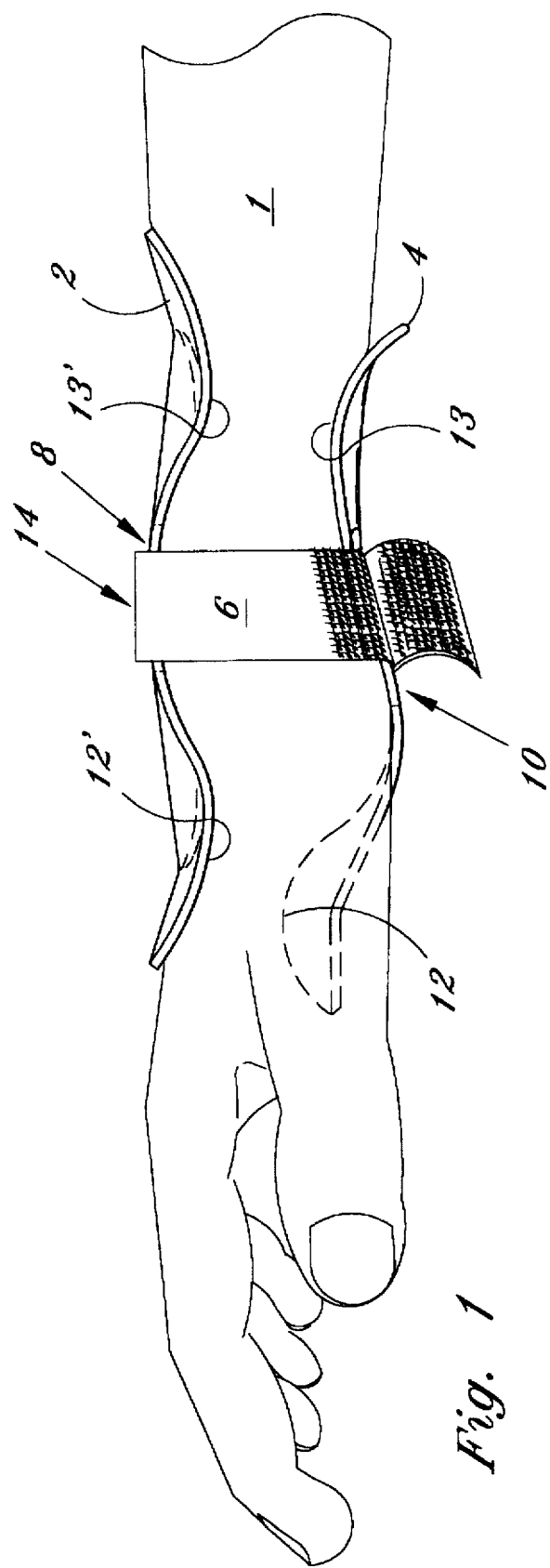
FIG. 1 is a side elevational view of the present invention on a human wrist.
Figure 7:
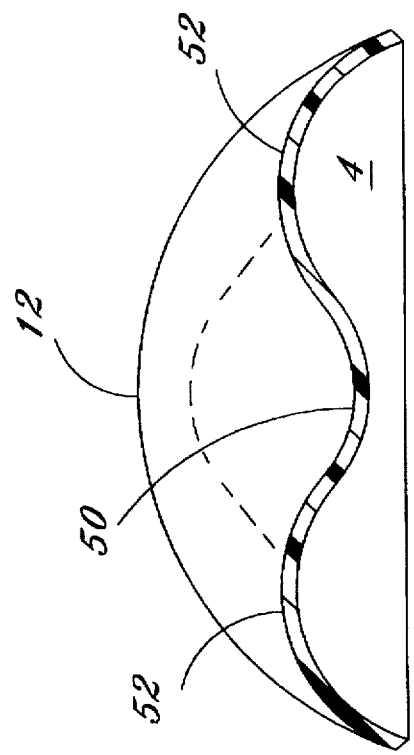

Referring now to the figures, and in particular FIG. 1, the preferred embodiment of the present invention, in general, includes top member 2, bottom member 4, and cinching strap 6 mounted on a human wrist 1.

Referring now to FIGS. 2a–2c and 3a–3c, top member 2 and bottom member 4 of the present invention are specially shaped, and made of a suitable material such as injection molded or heat formed pliable thermoplastic. Top member 2 and bottom member 4 are preferably transparent to allow observation of pressure points when the device is cinched in place, and to permit viewing of watches or jewelry.

Top member 2 includes arched portion 8 located near the center of top member 2, shown in FIG. 2b. Bottom member 4 includes arched portion 10 located near the center of bottom member 4, shown in FIG. 3b. Arched portions 8 and 10 are preferably each approximately ½ inch in height.

Bottom member 4 also has domed portion 12 located at one end as shown in FIGS. 3b and 3c. Dome portion 12 is preferably approximately 1½ inches in height.

Top member 2 includes aperture 20 which provides attachment points for cinching strap 6. Bottom member 4 provides apertures 22 for engaging cinching strap 6 when the invention is in use on a wrist. Cinching strap 6 is preferably made of any suitable material such as nylon, and having a suitable attaching means such as a hook and loop fastener. One end of cinching strap 6 is permanently attached through aperture 20 to top member 2 by a suitable means such as sewing a portion of strap 6 to itself to form a loop, as shown in FIG. 2a.

In an alternate embodiment shown in FIGS. 4a–5c, instead of apertures 20 and 22, hook and loop pads 16 and 18 are attached to top member 2 and bottom member 4 by any suitable means such as gluing. Cinching strap 6 is then held in place by attaching corresponding hook and loop areas to hook pads 16 and 18.

The functioning of both of the embodiments shown are the same with only the attachment method varying slightly. Therefore, like features are numbered the same on FIGS. 2a–3c and 4a–5c. The invention is described using two attachment means as examples only and is not intended to be an exhaustive representation of attachment methods. The two means shown are being used for example only, other attachment methods are contemplated by this invention.

Referring again to FIGS. 1–5c, when the present invention is in use, bottom member 4 is positioned under a human wrist and top member 2 is positioned over the wrist. Dome portion 12 of bottom member 4 fits comfortably in the palm of the hand. Arched portion 10 of bottom member 4 is positioned under and arches away from wrist bending point 14. Arched portion 8 of top member 2 is positioned over and arches away from wrist bending point 14.

Hook and loop cinching strap 6 is wrapped around wrist 1, top member 2, and bottom member 4. Cinching strap 6 is held in place on top member 2 and bottom member 4 by either engaging hook pads 16 and 18, as shown in FIGS. 4a–5c, or is permanently attached to top member 2 at aperture 20 and wrapped through apertures 22 in bottom member 4, as shown in FIGS. 2a–3c. Once cinching strap 6 is wrapped around the wrist and around top member 2 and bottom member 4, it is attached to itself using a suitable fastening method, such as a hook and loop method as shown in FIG. 1.

Cinching strap 6 firmly clamps opposing arched portions 8 and 10 toward the wrist and toward each other in spring-like fashion. The force of cinching strap 6 on arched portions 8 and 10 causes portions 12 and 13 on bottom member 4 and opposing portions 12' and 13' on top member 2 to exert clamping forces on corresponding sections of wrist 1. The clamping forces resulting from portions 12 and 12' and 13 and 13' are applied to the wrist in front of and behind wrist bending point 14, as shown in FIG. 1. The clamping forces applied in front of and behind wrist bending point 14 effectively immobilize the wrist while permitting unrestricted movement of the fingers and use of the hand.

Apertures 20 and 22 and hook pads 16 and 18 are large enough to permit relative movement of top member 2 and bottom member 4 to adjust the device to different size wrists.

An alternate embodiment of bottom member 4 is shown in FIGS. 6a–6c and FIG. 7. Shaped portions 52 apply pressure to either side of the median nerve when the device is being worn. Shaped portion 50 forms a valley area below the median nerve. Valley area 50 prevents pressure from being applied to the median nerve. Raised areas 52 reverts pressure to areas on either side of the nerve. The combination of raised areas 52 and valley area 50 provides additional relief to the median nerve area and to injuries such as Carpal Tunnel Syndrome.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A brace for supporting a user's wrist comprising:

an elongated top member having a first end, a second end and an arched portion located between said first end and said second end, said arched portion adapted to be positioned on top of a bending point of a user's wrist and arched away from the bending point along the length of said elongated top member;

an elongated bottom member having a first end, a second end and an arched portion located between said first end an said second end, said arched portion adapted to be positioned on bottom of the bending point of a user's wrist and arched away from the bending point along the length of said elongated bottom member; and means for attaching said top member on top of a user's wrist and said bottom member on bottom of a user's wrist;

said means for attaching being movably connected between said first end and said second end of said top member, said means for attaching being movably connected between said first end and said second end of said bottom member;

wherein said means for attaching forcibly clamps said top member and said bottom member on a user's wrist thereby immobilizing a user's wrist.

2. A brace for supporting a user's wrist as claimed in claim 1, wherein said means for attaching is movably connected to said arched portion of said top member and said means for attaching is movably connected to said arched portion of said bottom member.

3. A brace for supporting a user's wrist as claimed in claim 1, wherein said bottom member further having a convex hemispherical dome located near said first end, said dome sized to comfortably fit into a palm of a user's hand.

4. A brace for supporting a user's wrist as claimed in claim 1, wherein said means for attaching being removably attached to said top member and said bottom member.

5. A brace for supporting a user's wrist as claimed in claim 4, wherein said means for attaching is a cinching strap having at least one hook and loop fastener.

6. A brace for supporting a user's wrist as claimed in claim 5, wherein said cinching strap being movably connected to said top member at a top member hook and loop pad and said cinching strap being movably connected to said bottom member at a bottom member hook and loop pad.

7. A brace for supporting a user's wrist as claimed in claim 1, wherein said top member and said bottom member are transparent.

8. A brace for supporting a user's wrist as claimed in claim 1, wherein said top member and said bottom member are made of thermoplastic and preformed in anatomically conforming configurations.

9. A brace for supporting a user's wrist as claimed in claim 1, wherein said means for attaching clamps said first end of said top member toward said first end of said bottom member, and said second end of said top member toward said second end of said bottom member wherein the brace is adapted to be positioned so pressure results in front of the bending point and behind the bending point of a user's wrist thereby immobilizing a user's wrist.

10. The brace of claim 3 further comprising;

two parallel elongated raised portions located on said bottom member between said convex hemispherical dome and said arched portion;

an elongated valley portion on said bottom member located between said two raised portions, wherein said raised portions are adapted to be positioned parallel to a longitudinal axis of the user's wrist and said valley portion is adapted to be positioned near a central portion of a user's wrist thereby resulting in an alleviation of pressure from the central portion of the user's wrist.

* * * * *